United States Patent [19]

Hanotier et al.

[11] 4,002,656

[45] Jan. 11, 1977

[54] PROCESS FOR THE SELECTIVE OXIDATION OF PARAFFINIC HYDROCARBONS

[75] Inventors: Jacques Daniel Victor Hanotier, Uccle; Philippe Jean Andre Charles Camerman, Wesembeek-Oppem, both of Belgium

[73] Assignee: Labofina S. A., Brussels, Belgium

[22] Filed: May 16, 1975

[21] Appl. No.: 578,361

Related U.S. Application Data

[63] Continuation-in-part of Ser. No. 141,987, May 10, 1971, abandoned.

[30] Foreign Application Priority Data

May 18, 1970 United Kingdom ............ 23897/70

[52] U.S. Cl. .................. 260/406; 260/465.1; 260/597 R; 260/593 H; 260/488 R; 260/448 F; 260/465.4; 260/465.8 R
[51] Int. Cl.$^2$ ............ C07C 121/14; C07C 121/30; C09F 7/02
[58] Field of Search ........ 260/465.1, 597 R, 593 H, 260/406, 488 R, 488 F, 465.4, 465.8 R

[56] References Cited

UNITED STATES PATENTS

| | | |
|---|---|---|
| 2,265,948 | 12/1941 | Loder ................ 260/451 |
| 2,920,087 | 1/1960 | Hay ................. 260/406 |
| 3,196,182 | 7/1965 | Cox ................. 260/597 |
| 3,351,657 | 11/1967 | Duncanson ............ 260/530 |
| 3,758,557 | 9/1973 | d'Ostrowick ........... 260/488 F |

OTHER PUBLICATIONS

Bigot et al., *Rec. Trav. Chim.* 84 (1965), pp. 1243–1246.

*Primary Examiner*—Winston A. Douglas
*Assistant Examiner*—John F. Niebling

[57] ABSTRACT

A process for the oxidation, in the presence of a cobalt salt, of straight-chain paraffinic compounds of general formula

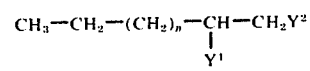

wherein $n$ is an integer from 1 to 16 inclusive, $Y^1$ is hydrogen or a substituent selected from the group consisting of X, CN, COOR and OCOR, wherein X is a halogen and R a hydrocarbon radical containing from 1 to 6 carbon atoms inclusive and $Y^2$ is selected from the group consisting of $Y^1$, $CHX_2$ and $CX_3$, and wherein $Y^1$ is hydrogen when $Y^2$ is $CX_3$ or is X when $Y^2$ is selected from the group consisting of $CX_3$ and $CHX_2$, with the selective formation of monoketones, having the same number of carbon atoms as the starting compound and of the general formula:

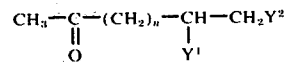

wherein $n$, $Y^1$ and $Y^2$ are as defined above, the process comprising contacting said paraffinic compounds with a cobalt salt having a trivalent cobalt to the total cobalt ratio between 0.5 and 1.0, based on metal cobalt, the concentration of said cobalt salt being at least 0.05 mole per liquid liter of reaction mixture, at a temperature between 20° and 120° C., and in the presence of molecular oxygen.

17 Claims, No Drawings

PROCESS FOR THE SELECTIVE OXIDATION OF PARAFFINIC HYDROCARBONS

BACKGROUND OF THE INVENTION

This application is a continuation-in-part of our co-pending application Ser. No. 141,987 filed May 10, 1971 and now abandoned.

The present invention relates to a process for the selective oxidation in the liquid phase of straight-chain paraffinic compounds of general formula

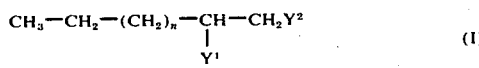  (I)

wherein $n$ is an integer from 1 to 16 inclusive, $Y^1$ and $Y^2$ are hydrogen atoms and/or substituents, with the preferential formation of monoketones of general formula

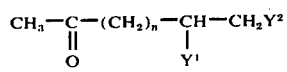

wherein $n$, $Y^1$ and $Y^2$ are defined above.

For the sake of brevity, the methyl group at the end of the chain opposite to that substituted with $Y^1$ and $Y^2$ (or any of both methyl groups when $Y^1$ and $Y^2$ are hydrogen) will be referred to hereinafter as "terminal methyl group" and, similarly, the term "methylketone" will refer to any compound having the general formula (II), even those where $Y^1$ and $Y^2$ are functional groups.

Many works have already been devoted to the liquid phase oxidation of paraffinic compounds, especially of straight-chain paraffinic hydrocarbons, by molecular oxygen, in the presence of catalysts or not. With such hydrocarbons, the required temperatures are generally between 100° and 200° C. and there is obtained a mixture of fatty acids, having less carbon atoms than the starting hydrocarbons, and a variety of neutral products, such as for example ketones, alcohols, esters, peroxides, hydroperoxides. Extensive breaking of the carbon chain occurs during these reactions with the consequence that the yield in any specific product is low. The conclusion of these prior works was that straight-chain paraffinic hydrocarbons are almost exclusively oxidised at the methylene groups in statistical manner within the chain, without any selectivity, and this conclusion is in agreement with those resulting from chlorination, nitration and other substitution reactions.

In the case of paraffinic compounds already substituted by a functional group, some orientation is observed in such reactions: with most substituents, e.g., $CH_2Cl$, $CCl_3$, CN, COX, COOR (where X is a halogen and R stands for hydrogen or a hydrocarbon radical), the carbon atom at the alpha position relative to the substituent is strongly deactivated and substitution preferentially occurs at the beta carbon atom.

But, for industrial purposes, it is particularly advantageous that the oxidation of paraffinic compounds may be directed to the preferential formation of compounds of one kind and, still more preferably, to a compound oxidised near the end of the carbon chain, e.g., in alpha position relative to a terminal methyl group as defined above.

SUMMARY OF THE INVENTION

This invention has for an object a process whereby this double selectivity is fulfilled and achieves the following advantages;

the oxidation of the paraffinic compounds proceeds with selective formation of monoketones having the same number of carbon atoms as the starting compound, the cabonyl function is preferentially located at the alpha position relative to a terminal methyl group, both selectivities occur within a large temperature range, thus allowing adjustment of the reaction rate by adjusting the temperature, the cobalt salt is easily regenerated for re-use, the oxidation products can be easily recovered from the reaction mixture.

According to the present invention a process of the present invention for the oxidation in the liquid phase, in the presence of a cobalt salt, of straight-chain paraffinic compounds of general formula:

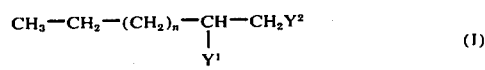  (I)

wherein $n$ is an integer from 1 to 16 inclusive, $Y^1$ is a hydrogen atom or a substituent such as X, CN, COOR, OCOR, where X is a halogen atom and R is a hydrocarbon radical, containing from 1 to 6 carbon atoms inclusive, and $Y^2$ is $Y^1$, $CHX_2$ or $CX_3$, $Y^1$ being a hydrogen atom when $Y^2$ is $CX_3$ or being X when $Y^2$ is $CX_3$ or $CHX_2$, with the selective formation of monoketones, having the same number of carbon atoms as the starting compound, of the general formula:

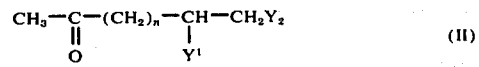  (II)

wherein $n$, $Y^1$ and $Y^2$ are as defined above, the process comprises contacting the paraffinic compounds with a cobalt salt having a trivalent cobalt to total cobalt ratio between 0.5 and 1.0, based on metal cobalt, the concentration of said cobalt salt being at least 0.05 mole per liter of reaction mixture, at a temperature between 20° and 120° C., and in the presence of molecular oxygen. The oxidation may be carried out at a partial pressure between 0.1 and 50, preferably between 1 and 10, atmospheres.

The cobalt salt used may be a salt of a carboxylic acid containing 2 to 4 carbon atoms.

It has been observed that in these conditions, not only the oxidation of the paraffinic compound is directed to the formation of methylketones, but, moreover, the rate may be controlled by varying the reaction temperature and without adding any activator, without detrimental variation of the selectivity. Thus, the strong acidic activators or boron trifluoride disclosed in U.S. Pat. No. 3,758,557 are unnecessary.

The process of the invention may be applied to any paraffinic compound as defined above by formula (I) and the oxidation selectivity at the alpha position relative to a terminal methyl group is observed irrespective of the chain length of the starting compound.

In carrying out the invention, it is not always essential to use a solvent for the process of the invention to be carried out in the liquid phase. In some cases, the cobalt salt is soluble in the paraffinic substrate and the reaction can take place in the solution thus obtained. However, where the cobalt salt is not very soluble in the substrate, it is preferable to use a solvent in which both the substrate and the cobalt salt are soluble, this solvent being substantially inert against oxidation in the reaction conditions. The lower fatty acids containing from 2 to 4 carbon atoms and their mixtures may be used to fulfill these conditions. Among these solvents, acetic acid is particularly advantageous.

The process of the invention may also be applied when the reaction mixture comprises two phases: on one hand, the liquid paraffinic compound to be oxidised and, on the other hand, a solution of the cobalt salt in a solvent in which said paraffinic compound is not completely soluble. For example, the paraffinic compound may be emulsified with an aqueous solution of the cobalt salt or with a solution of the salt in a mixed solvent consisting of water and a lower fatty acid. With such a system, the paraffinic substrate can be used to extract the reaction products, which are thus protected against subsequent degradation.

Among the cobalt salts that can be used in the present invention, those of carboxylic acids are particularly suitable as they are satisfactorily soluble in both organic and aqueous media. Although the cobalt salt of any carboxylic acid may be used, the salts of the lower fatty acids containing from 2 to 4 carbon atoms are particularly advantageous, as their cobaltic form is readily prepared from the corresponding cobaltous form. For example, cobaltic acetate can be prepared by co-oxidation of cobaltous acetate and acetaldehyde in acetic acid in the presence of oxygen.

In order to ensure efficient and selective oxidation by the process of the present invention, the cobalt salt is used in relatively high concentration, i.e., at least 0.05 mole per liter, with a trivalent cobalt to total cobalt ratio, i.e., $K = Co(III)/Co(III) + Co(II)$, higher than 0.5, based on metal cobalt. When the concentration of the cobalt salt is below said limit, the reaction rate is too low to be of practical application. Moreover, although the unique selectivity of the process for methylketones may be already observed at cobalt concentrations as low as 0.01 mole per liter, the best results are obtained when the cobalt concentration is at least 0.05 mole per liter and still preferably at least 0.1 mole per liter. As those skilled in the art will appreciate, the cobalt concentration to be used in any specific case is determined by practical and economical considerations, the upper limit being the concentration at which the reaction mixture is saturated. The specific examples presented herein-below demonstrate that significant increases in conversion, with continuing improvement in selectivity, are obtained as the cobalt concentration increases above 0.2, and especially above 0.3.

As the reaction proceeds, the cobaltic portion of the cobalt salt is progressively reduced in the cobaltous form thereof so that both species are always present in the reaction mixture. We have found, and this feature is an important aspect of the present invention, that when the cobalt salt is used in relatively high concentration as specified above, its oxidizing activity is the more pronounced as the K ratio is higher, this activity becoming almost negligible when both cobalt forms are present in equivalent amounts. In this case, i.e., when K is nearly 0.5 or lower, not only the reaction rate is drastically depressed and the process is no longer suitable for industrial application, but the reaction loses its selectivity, i.e., the production of ketones is lowered in favor of a non-selective production of acids. If temperature is increased to restore the reaction rate, the loss of selectivity is also increased. Therefore, in order to obtain a high yield in methylketones, the K ratio should be kept between 0.5 and 1 and preferably between 0.6 and 1. From the exemplary embodiments folllowing hereinafter, it is seen that the preferred K ratio is above about 0.8 and especially above about 0.9. For this condition to be fulfulled, the cobaltous salt formed during the reaction must be continuously reoxidised. For this purpose, different methods may be used. For example, the cobaltous salt may be oxidised by anodic oxidation or by chemical means, e.g., by co-oxidation compound, such as acetaldehyde, benzaldehyde or methylethylketone. A particularly convenient process is to continuously inject acetaldehyde into the reaction mixture.

An important and unexpected feature of the present invention is the discovery that, in the conditions as specified above, the unique selectivity of the process is still observed at temperatures as high as 120° C., thus at temperatures close to those used in many conventional non-selective processes. This feature is of great advantage as the optimum temperature for carrying out the desired oxidation may be selected in a relatively large range, i.e., between 20° and 120° C., according to the reactivity of the substrate, its solubility in the reaction medium and other specific aspects. In most cases, however, the optimum temperature will be between 30° and 100° C., and still more frequently between 50° and 70° C.

In order to form methylketones selectively by the process of the invention, it is necessary to operate in the presence of a gaseous phase containing molecular oxygen and to ensure vigorous stirring for rapid diffusion of the latter in the liquid phase. This gaseous phase may consist in pure oxygen or in a mixture of oxygen with other gases inert in the conditions of the reaction; air may be used, for example. The oxygen partial pressure may lie between 0.1 and 50 atmospheres. In particular cases, it is possible to apply pressures outside this range. For example, a pressure lower than 0.1 atmosphere may be sufficient, provided that particularly efficient stirring be ensured. On the other hand, pressures higher than 50 atmospheres may be applied, but these do not result in an improvement such as to justify additional plant investment. In most cases, an oxygen pressure of 1 to 10 atmospheres will advantageously be applied to secure a high proportion of ketones.

The products prepared by the process of the invention have many industrial uses. The ketones are used as solvents plasticizers and aroma. Upon hydrogenation, they are converted into secondary alcohols which are used in the manufacture of surface-active agents. By further oxidation, they yield fatty acids of widespread use. The oxidation products obtained from already substituted paraffinic compounds can be used for the production of difunctional derivatives, such as diacids and amino-acids which are used for the manufacture of polyamides.

DETAILED DESCRIPTION OF SPECIFIC EMBODIMENTS

The invention will now be further described and illustrated with reference to the following Examples:

EXAMPLE 1

This example illustrates the oxidation of n-heptane into monoketones and more particularly into 2-heptanone.

A solution containing 0.33 mole/liter of cobalt acetate in acetic acid with a K ratio of 0.93 was heated to 60° C. Heptane was then added up to a final concentration of 0.80 mole/liter. The resulting solution was stirred at the same temperature in the presence of oxygen at atmospheric pressure. After 30 minutes, the reaction was stopped by reducing the cobaltic ions with an aqueous solution of a ferrous salt.

The reaction products were extracted by either, then fractionated into acidic and non-acidic components by treatment of the extract with alkali and the resulting fractions were analyzed separately by Vapour-phase chromatography.

It was shown that 2.9% of the starting heptane had been converted to yield the following products whose relative proportions are given as molar percentages:

| heptanones | : | 63% (isomer 2: 79%; 3: 15%; 4: 6%) |
| heptanols | : | 15% (isomer 1: 0%; 2: 70%; 3:22%; 4: 8%) |
| acids | : | 17% |
| others | : | 5% |

It is apparent that by working in the conditions of the present invention, heptane is mainly converted into monoketones with selective production of 2-heptanone. It is noteworthy that by statistical oxidation of the methylene groups, the relative proportion of 2-heptanone should be only 40% instead of 79% as in the present example.

EXAMPLE 2

This Example illustrates the oxidation of n-heptane in the presence of a solvent other than acetic acid.

The procedure of Example 1 was repeated except that propionic acid was substituted for acetic acid.

The reaction products were shown to be mainly monoketones, with a 81% proportion of 2-heptanone.

EXAMPLE 3

This example illustrates the oxidation of n-heptane in a biphasic system.

83 ml. of a solution containing 0.75 mole/liter of cobalt acetate in a mixed solvent consisting of water (40 vol. %) and acetic acid (60 vol. %) and having a K ratio of 0.97 were heated to 60° C. To this solution were then added 17 ml. of heptane most of which remained as a distinct phase. The resulting biphasic mixture was vigorously stirred at the same temperature in the presence of oxygen at atmospheric pressure. After 6 hours, the reaction mixture was treated and analyzed as in Example 1.

It was thus shown that 54% of the oxidation products consisted in monoketones, with a 77% proportion of 2-heptanone.

EXAMPLE 4

This Example illustrates the oxidation of a paraffinic compound by a carboxylic salt of cobalt in the absence of any solvent.

A solution containing 0.30 mole/liter of cobalt pelargonate in pure n-heptane and having a K ratio of 0.80 was kept at 60° C., while stirring, in the presence of oxygen at atmospheric pressure. After 3 hours, the reaction mixture was treated and analyzed as in Example 1.

It was thus shown that heptane had been mainly converted into monoketones with a 79% of 2-heptanone.

EXAMPLE 5

This Example illustrates the oxidation of n-decane into monoketones, and more particularly into 2-decanone.

A solution containing 0.22 mole/liter of cobalt acetate in acetic acid and with a K ratio of 0.91 was heated to 60° C. Decane was then added up to a final concentration of 0.5 mole/liter and the same procedure as in Example 1 was followed.

It was thus shown that 3.7% of the starting decane had been converted to yield the following products whose relative proportions are given as molar percentages:

| decanones | : | 54% (isomer 2: 63%; 3: 12%; 4 + 5: 25%) |
| decanols | : | 15% (isomer 2: 53%; 3: 13%; 4 + 5: 34%) |
| acids | : | 24% |
| others | : | 7% |

By statistical oxidation of the methylene groups, the relative proportion of 2-decanone should be only 25% instead of 63% as in the present Example.

EXAMPLE 6

This example illustrates the selective oxidation of the methyl ester of enanthic acid into oxo-derivatives and more particularly into 6-oxo-enanthate.

A solution containing 0.39 mole/liter of cobalt acetate in acetic acid and having a K ratio of 0.91 was heated to 60° C. Methyl enanthate was then added up to a final concentration of 1 mole/liter and a procedure similar to that of Example 1 was followed.

It was thus shown that 2.6% of the starting ester had been converted to yield the following products whose relative proportions are given as molar percentages:

| oxo-enanthates | : | 75% (isomer 6: 72%; 5: 16%; 4: 11%; 3 + 2: 1%) |
| hydroxyenanthates | : | 9% (isomer 6: 85%; 5: 15%; 4 + 3 + 2: —) |
| Acids | : | 7% |
| Others | : | 9% |

By statistical oxidation of the methylene groups, the relative proportion of 6-oxo-enanthate should be only 20% instead of 72% as in the present Example.

EXAMPLE 7

This Example illustrates the selective oxidation of several straight-chain paraffinic compounds of general formula:

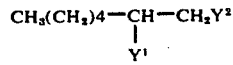

These compounds were oxidised in the same conditions as in Example 6 and in each case they were mainly converted into monoketones (oxo-derivatives) whose relative proportions are given in the following Table.

| | | Relative proportions of the oxo-derivatives | | | | | | |
|---|---|---|---|---|---|---|---|---|
| | | C — C — C — C — C CY¹ — CY² | | | | | | |
| Y¹ | Y² | 7 | 6 | 5 | 4 | 3 | 2 | 1 |
| H | Cl | — | 75 | 16 | 5 | | 5 | — |
| Cl | H | | 73 | 17 | 8 | 2 | — | — |
| H | OCOCH₃ | — | 69 | 13 | | 16 | 2 | — |
| OCOCH₃ | H | — | 74 | 18 | 7 | 1 | — | — |
| H | C≡N | — | 74 | 10 | | 16 | | — |

It can be seen that the proportion of the 6-oxo isomer is generally more than three times higher than calculated for a statistical oxidation of the methylene groups.

EXAMPLE 8

This Example illustrates the selective oxidation of the methyl ester of pelargonic acid into oxo-derivatives and more particularly into the 8-oxo-derivative. The conditions and procedure were the same as in Example 6. It was thus shown that 2.2% of the starting ester had been converted to yield the following products whose relative proportions are given as molar percentages.

| oxopelargonates | : | 75% (isomer 8: 58%; 7: 11%; 6: 10%; 5 + 4: 19%; 3 + 2: 2%) |
|---|---|---|
| hydroxypelargonates | : | 16% (isomer 8: 58%; 7: 11%; 6: 10%; 5 + 4: 13%; 3 + 2: —) |
| acids | : | 6% |
| others | : | 3% |

By statistical oxidation of the methylene groups, the relative proportion of 8-oxopelargonate should be only 14%, instead of 50% as in the present Example.

EXAMPLE 9

This Example illustrates the effect of temperature on the selectivity of the oxidation of n-heptane and n-decane.

Unless otherwise stated, the procedure used was that of Example 1.

The results obtained are quoted in Table I. These show that, with both hydrocarbons, the selectivity of oxidation on alpha position relative to a terminal methyl group remains definitely higher than statistical (40% for heptane and 25% for decane), even at a temperature as high as 120° C.

TABLE I

| Hydrocarbon | Temperature (°C) | Hydrocarbon Concentration (mole/liter) | Cobalt Concentration (at g/liter) | Reaction Time (min.) | Monoketones (relative % in isomers) | | | |
|---|---|---|---|---|---|---|---|---|
| | | | | | 2 | 3 | 4 | 5 |
| n-heptane | 40 | 1.12 | 0.33 | 60 | 81 | 13 | 6 | |
| | 60 | 1.12 | 0.33 | 15 | 79 | 15 | 6 | |
| | 80 | 1.12 | 0.33 | 15 | 78 | 15 | 7 | |
| | 100 | 1.12 | 0.33 | 15 | 76 | 17 | 7 | |
| | 120 | 1.12 | 0.33 | 15 | 66 | 24 | 10 | |
| n-decane | 40 | 0.59 | 0.20 | 360 | 65 | 12 | | 23 |
| | 60 | 0.50 | 0.20 | 30 | 63 | 12 | | 25 |
| | 100 | 0.50 | 0.20 | 15 | 59 | 15 | | 26 |

EXAMPLE 10

This Example illustrates the influence of cobalt concentration on the rate and the selectivity of the oxidation of n-heptane.

Different experiments were performed from cobalt solutions of different concentrations each having a K ratio of 0.95. The general procedure was the same as in Example 1, except that the temperature was 100° C. and the reaction time 180 min.

The results were as follows:

| Co concentration (at g/liter | 0.01 | 0.02 | 0.05 | 0.1 | 0.2 | 0.3 | 0.5 |
|---|---|---|---|---|---|---|---|
| Conversion of heptane in oxidation products (%) | 0.4 | 0.7 | 1.1 | 1.8 | 3.2 | 3.8 | 6.2 |
| Relative proportion of 2-isomer in heptanones (%) | 58 | 58 | 61 | 66 | 67 | 69 | 71 |

These data clearly show that both the rate and the selectivity of the reaction are highly dependent on the concentration of cobalt, the best results being obtained for the higher cobalt concentration.

EXAMPLE 11

This Example illustrates the influence of the K ratio on the reaction rate and the selective production of ketones from n-heptane.

Different experiments were performed from cobalt solutions having different K ratios. In each of them, however, the concentration of trivalent cobalt was the same (about 0.28 at g/liter). Unless otherwise stated, the procedure was the same as in Example 1. The results of these experiments are summarized in Table II.

TABLE II

| Temperature (° C.) | 60 | 100 |
|---|---|---|
| Initial K | | |

TABLE II-continued

| Temperature (° C.) | 60 | | | | | 100 | | | |
|---|---|---|---|---|---|---|---|---|---|
| Ratio | 0.93 | 0.60 | 0.50 | 0.50 | 0.50 | 0.96 | 0.60 | 0.50 | 0.50 |
| Reaction time (hours) | ½ | ½ | ½ | 6 | 18 | ¼ | ¼ | ¼ | 3 |
| Conversion of heptane in oxidation products (%) | 2.9 | 0.5 | 0 | 0.3 | 0.9 | 3.1 | 1.7 | 0.6 | 3.7 |
| Yield in heptanones(1) | 63 | 49 | 0 | 52 | 41 | 42 | 44 | 30 | 19 |
| Relative proportion of 2-isomer in heptanones (%) | 79 | 78 | 0 | 80 | 78 | 76 | 75 | 72 | 71 |

(1) Mole % monoketones in oxidation products.

These results show that a decrease of the K raio results in:

(1) a decrease of the reaction rate, this decrease being the more pronounced as said ratio tends toward 0.5. For example, at 100° C. with a K ratio of 0.6, the reaction rate is three times higher than with a K ratio of 0.5.

(2) a decrease in the production of monoketones, more particularly of 2-heptanone, this decrease being the more pronounced as said ratio decreases below 0.6 and tends towards 0.5.

EXAMPLE 12

This Example describes a practical method for maintaining a high K ratio during the reaction by continuously injecting acetaldehyde in the reaction mixture.

A 1 l. stainless steel autoclave equipped with a mechanical agitating device, a heating jacket, a cooling coil, a gas inlet tube, a valved vent and means for injecting and withdrawing liquids, is charged with 500 ml. of an acetic solution of cobalt acetate having a cobalt concentration of 0.60 mole/liter and a K ratio of 0.95. After pressurization to 10 kg/cm², the mixture was stirred and heated up to 50° C., while passing air thereinto at a rate of 100 liters per hour. Once the temperature of 50° C. was reached, cobalt acetate and heptane, both dissolved in acetic acid, were injected separately into the autoclave. The mixture of these solutions (influent) contained 0.60 mole/liter of cobalt acetate, with a K ratio of 0.95, and 0.75 mole/liter of n-heptane. The flow rate of this influent was so adjusted that its mean residence time in the reactor was 30 minutes, the volume in the latter being maintained to 500 ml. by continuously withdrawing the reaction mixture (effluent) through a control valve. Once the steady state was reached, samples of the effluent were taken off to be treated and analyzed as in Example 1.

Another experiment was carried out in the same conditions, except that acetaldehyde was present in the influent at a concentration of 0.21 mole/liter.

The results of both experiments are compared in Table III.

TABLE III

| Acetaldehyde | − | + |
|---|---|---|
| K ratio in the effluent | 0.82 | 0.98 |
| Conversion of heptane into oxidation products (%) | 2.8 | 8.2 |
| Yield in heptanones(1) | 73 | 67 |
| Relative proportion of 2-isomer in heptanones (%) | 83 | 75 |

(1) Mole % of monoketones in oxidation products.

What is claimed is:

1. A process for the oxidation of aliphatic compounds of the formula:

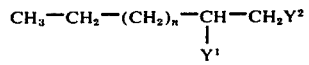

wherein n is an integer from 1 to 16 inclusive, wherein $Y^1$ is hydrogen or a substituent selected from the group consisting of X, CN, COOR and OCOR, wherein X is a halogen and R is an alkyl radical containing from 1 to 6 carbon atoms inclusive, wherein $Y^2$ is selected from the group consisting of $Y^1$, $CHX_2$ and $CX_3$ and wherein $Y^1$ is hydrogen or X when $Y^2$ is $CX_3$ and $Y^1$ is X when $Y^2$ is $CHX_2$, to produce selective formation of monoketones having the same number of carbon atoms as the starting compound and being of the formula:

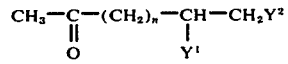

wherein n, $Y^1$ and $Y^2$ are as defined above, the process comprising contacting a feed consisting essentially of said aliphatic compounds in the liquid phase with a catalyst wherein the active agent in said catalyst consists essentially of a mixture of divalent and trivalent cobalt ions having a combined concentration of from 0.05 mole per liter of reaction mixture to the saturation level of the reaction mixture, at a temperature between 30° and 100° C., in the presence of molecular oxygen and in the absence of an activator, said mixture of divalent and trivalent cobalt ions having a Co(III)/Co(III) + Co(II) ratio of between 0.8 and 1.0.

2. The process of claim 1, wherein the oxidation is carried out at a partial pressure of said molecular oxygen between 0.1 and 50 atmospheres.

3. The process of claim 1, wherein the oxidation is carried out at a partial pressure of said molecular oxygen between 1 and 10 atmospheres.

4. The process of claim 1, wherein the concentration of said cobalt ions is at least 0.1 mole per liter of reaction mixture.

5. The process of claim 1, wherein said mixture of divalent and trivalent cobalt ions is present in the form of a cobalt salt of a fatty acid containing from 2 to 4 carbon atoms.

6. The process of claim 5, wherein said salt is the cobalt salt of acetic acid.

7. The process of claim 1, wherein the oxidation is carried out in the presence of a lower fatty acid containing from 2 to 4 carbon atoms or a mixture of such acids, as solvent.

8. The process of claim 7, wherein said solvent is acetic acid.

9. The process of claim 1, wherein said mixture of divalent and trivalent cobalt ions has a Co(III)/Co(III) + Co(II) ratio of between 0.9 and 1.0.

10. The process of claim 1, further comprising the step of continuously re-oxidizing divalent cobalt ion to trivalent cobalt ion concurrently with the oxidation of said aliphatic compounds.

11. The process as defined by claim 10, wherein said oxidation of the divalent cobalt ion is accomplished by addition of an oxidizing agent.

12. The process as defined by claim 11, wherein said oxidizing agent is acetaldehyde.

13. The process as defined by claim 1, wherein said reaction temperature is between 50° and 100° C.

14. The process as defined by claim 1, wherein said reaction temperature is between 50° and 70° C.

15. The process as defined by claim 1, wherein said process is carried out in the absence of an acidic activator having a dissociation constant greater than $5 \times 10^{-3}$ and boron trifluoride.

16. The process as defined by claim 1, wherein the concentration of said cobalt ions is at least 0.2 mole/liter.

17. The process as defined by claim 1, wherein the concentration of said cobalt ions is at least 0.3 mole/liter.

* * * * *